US00PP27985P2

(12) United States Plant Patent
Warren

(10) Patent No.: US PP27,985 P2
(45) Date of Patent: May 9, 2017

(54) MAPLE TREE NAMED 'JFS-KW249'

(50) Latin Name: *Acer truncatum*
Varietal Denomination: JFS-KW249

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 14/757,328

(22) Filed: Dec. 16, 2015

(51) Int. Cl.
*A01H 5/00* (2006.01)

(52) U.S. Cl.
USPC ..... Plt./224

(58) Field of Classification Search
USPC ..... Plt./224
See application file for complete search history.

*Primary Examiner* — Annette Para
(74) *Attorney, Agent, or Firm* — Klarquist Sparkman, LLP

(57) ABSTRACT

A variety of maple tree which combines a dense compact oval to broadly oval form with short internodes, very glossy foliage, and bright fall color

10 Drawing Sheets

Latin name of the genus and species of the plant claimed and variety denomination: *Acer truncatum* 'JFS-KW249'.

BACKGROUND OF THE INVENTION

In 1983, I initiated a program of selection and improvement in the species *Acer truncatum*. As part of this program, in March of 1988, I selected four seedlings growing in a cultivated area which I planted into a trial block on a nursery in Boring, Oreg. None of these seedlings have been patented. After several years of evaluation, I determined that one of these trees, which I designated *Acer truncatum* 'D' was the best in terms of foliage quality, form, and fall color. In the fall of 1994, I picked seed from this tree and sowed in a seedbed in the same nursery and raised 68 seedlings and subsequently selected only one, which I named 'KW-201ATR' (unpatented), and I planted it in February 2001 into another long term evaluation block in the same nursery. Over the next several years, I observed that 'KW-201ATR' had many of the characteristics that I was looking for in my selection program, notably stronger vigor combined with compact growth and good fall color. But it was not as compact as I desired and the fall color was not as bright as I desired. In October of 2002, I picked seed from 'KW-201ATR' and sowed it in a seedbed in the same Boring, Oreg. nursery. From this seed lot, I grew 43 trees which I evaluated until March 2007, at which time I selected and transplanted the best 18 trees, discarding the rest. These eighteen trees were grown on wider spacing for two more years and periodically evaluated, and in March of 2009 I selected and transplanted the best nine trees, into a long term evaluation block for final cultivar selection. Of these nine trees, I selected one tree which I named 'JFS-KW249' as the present invention. My attention was drawn to 'JFS-KW249' because it had the densest, compact form while maintaining good vigor and it developed a beautiful bright red fall color.

In August 2012 and again in August 2013, I directed the asexual propagation in Boring, Oreg. of my new variety by budding onto *Acer platanoides* rootstock.

From this propagation, I determined that the characteristics of my new variety are firmly fixed and all propagated plants have been identical to my new variety in every way observed.

SUMMARY OF THE INVENTION

This new cultivar possesses a unique combination of characteristics in that it combines a dense compact oval to broadly oval form with short internodes, very glossy foliage, and bright fall color.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
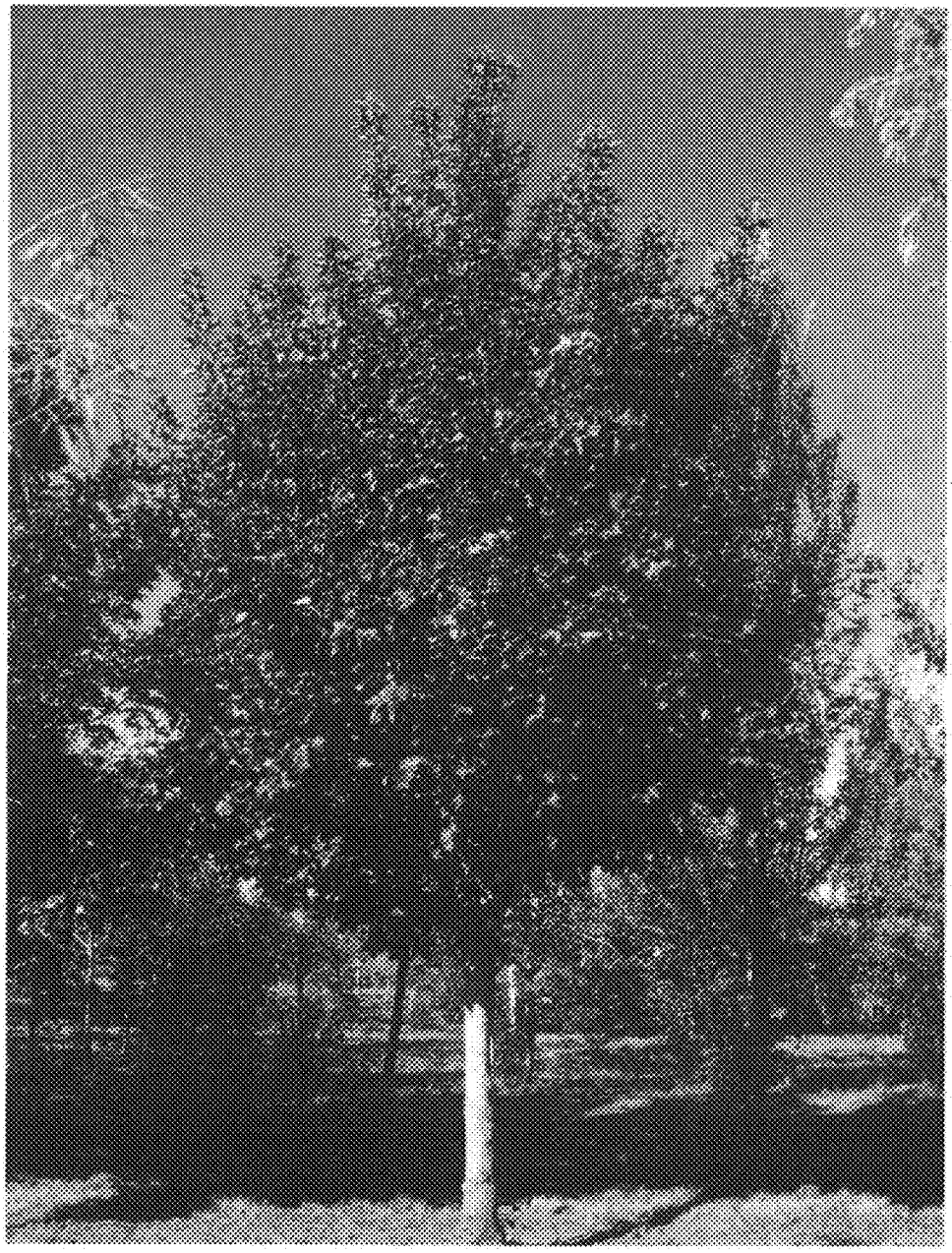
FIG. 1: Shows the original tree of my new variety at 13 years of age in summer foliage illustrating its oval to broadly oval growth habit and summer color of foliage.
Figure 2:
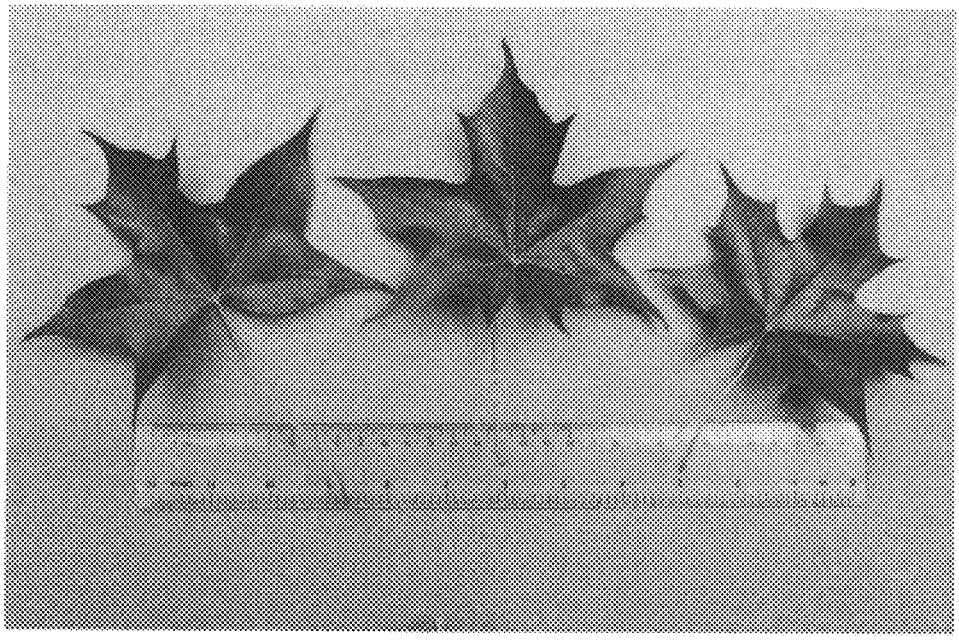
FIG. 2: Shows the upper surface of leaves in summer illustrating the color, shape and glossy sheen on a display board with a scale.
Figure 3:
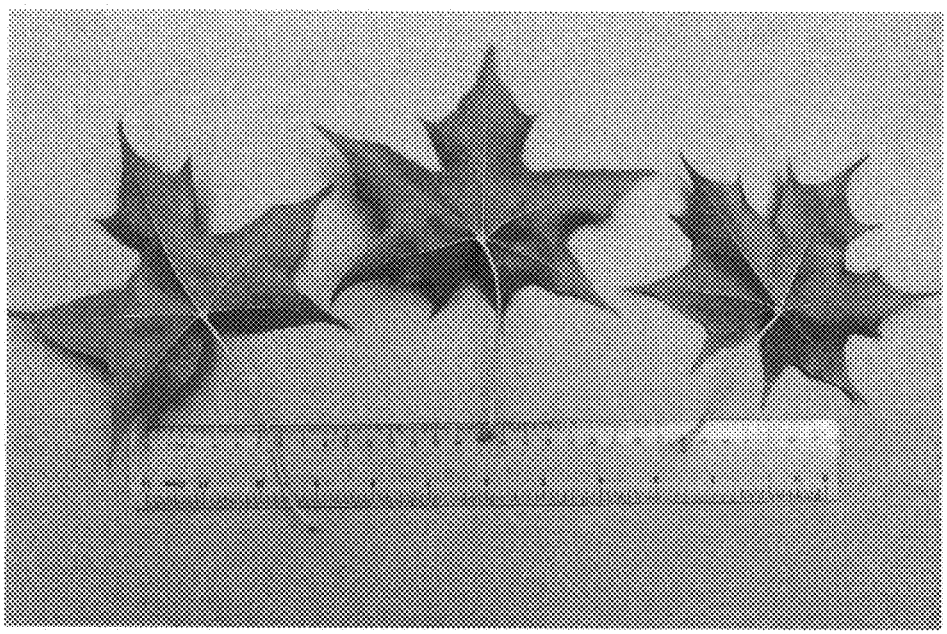
FIG. 3: Shows the lower surface of leaves in summer illustrating the color and shape on a display board with a scale.
Figure 4:
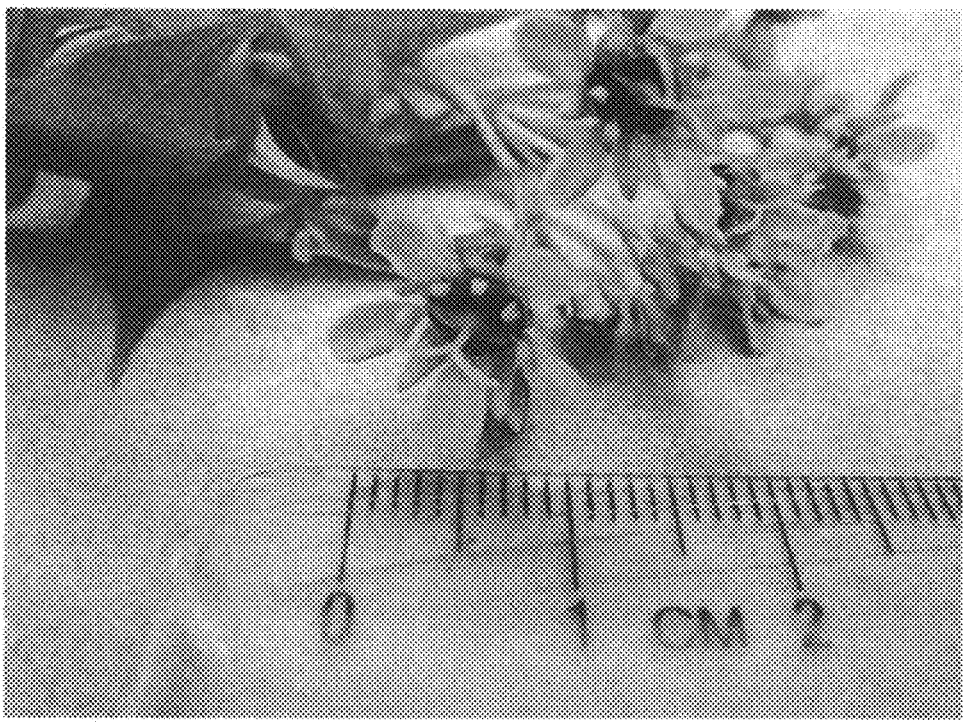
FIG. 4: Shows a corymb of female flowers in spring with a scale.
Figure 5:
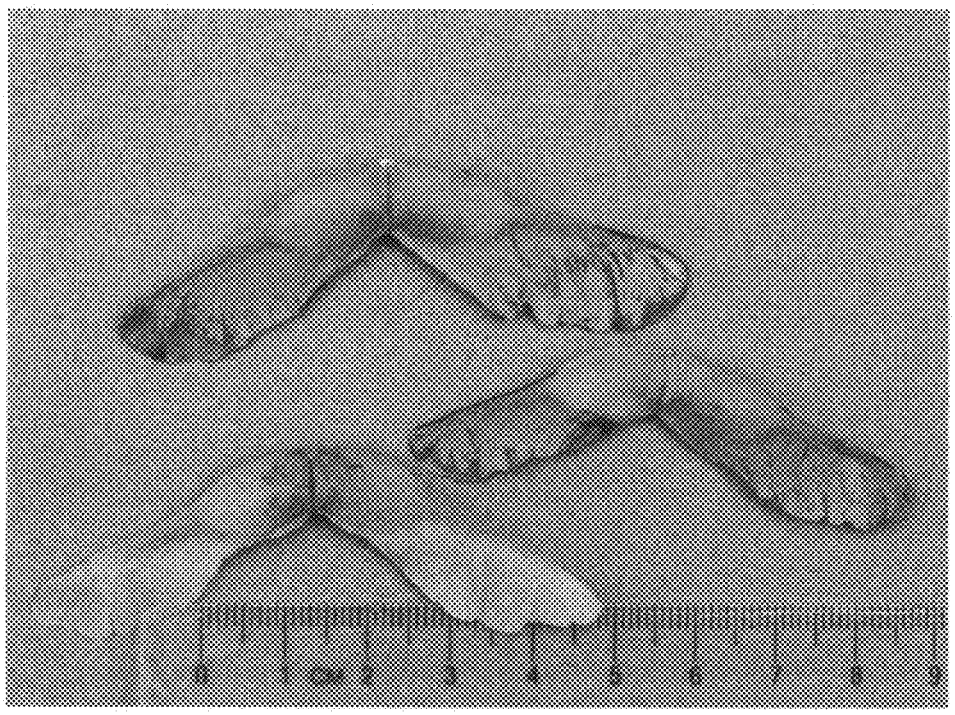
FIG. 5: Shows the samaras (with a scale) in autumn as they are ripening to maturity.
Figure 6:
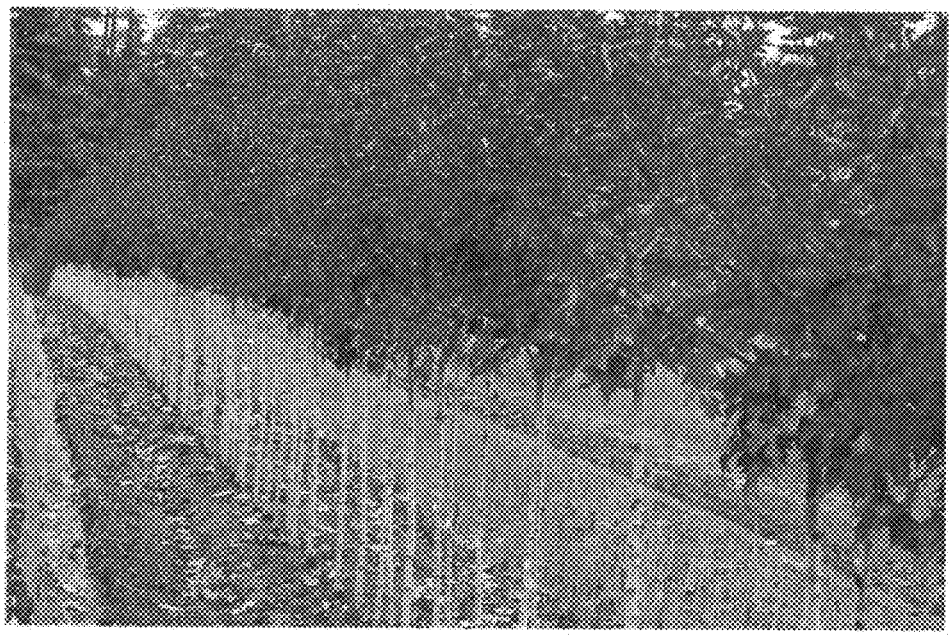
FIG. 6: Shows a vegetatively propagated nursery row of 2 year old trees in fall color.
Figure 7:
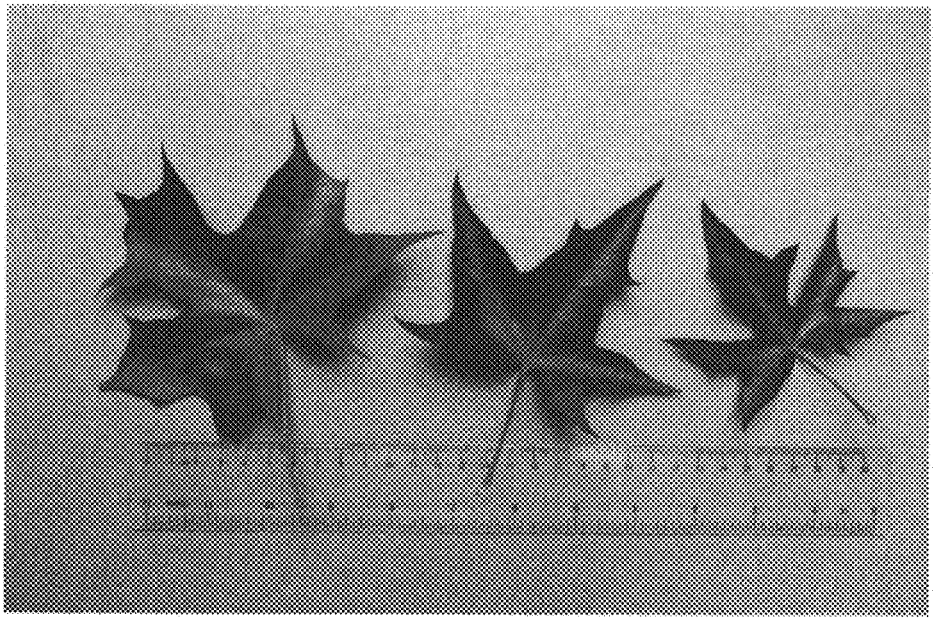
FIG. 7: Shows leaves in fall color on a display board with a scale.
Figure 8:
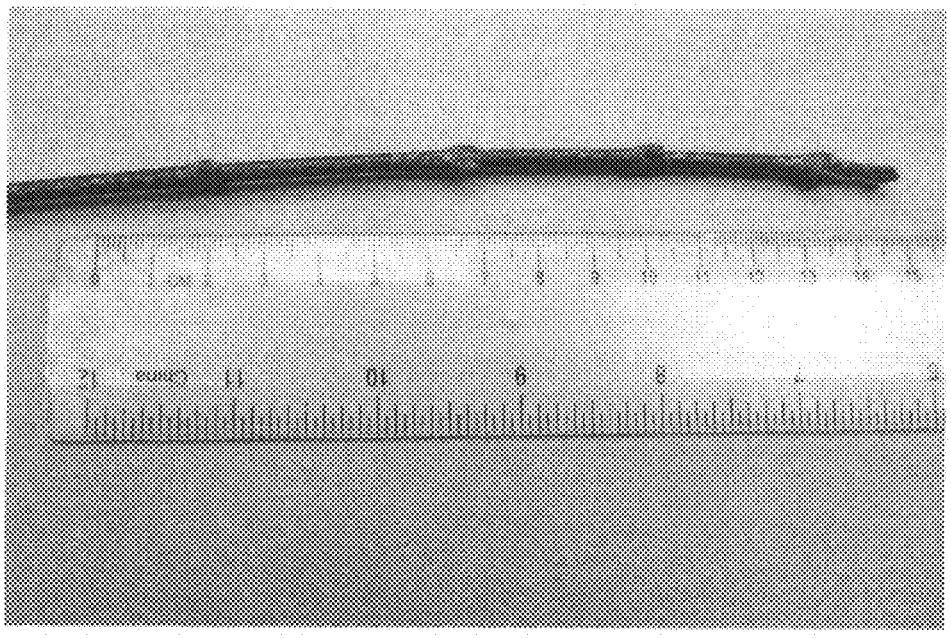
FIG. 8: Shows a winter twig and buds on a display board with a scale.
Figure 9:
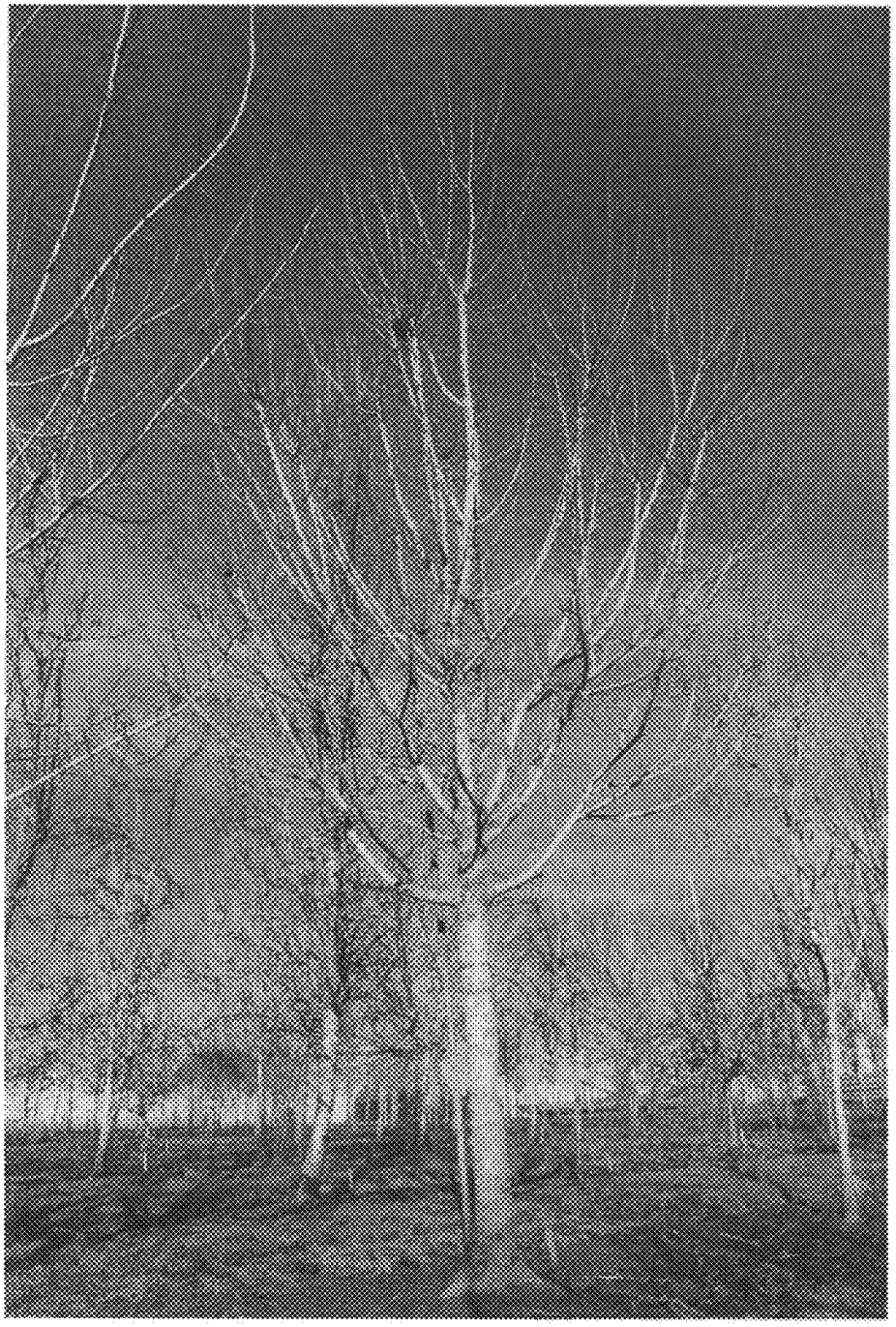
FIG. 9: Shows the original tree at 13 years of age during the winter dormant season illustrating the density of its branching and Oit's oval to broadly oval form.
Figure 10:
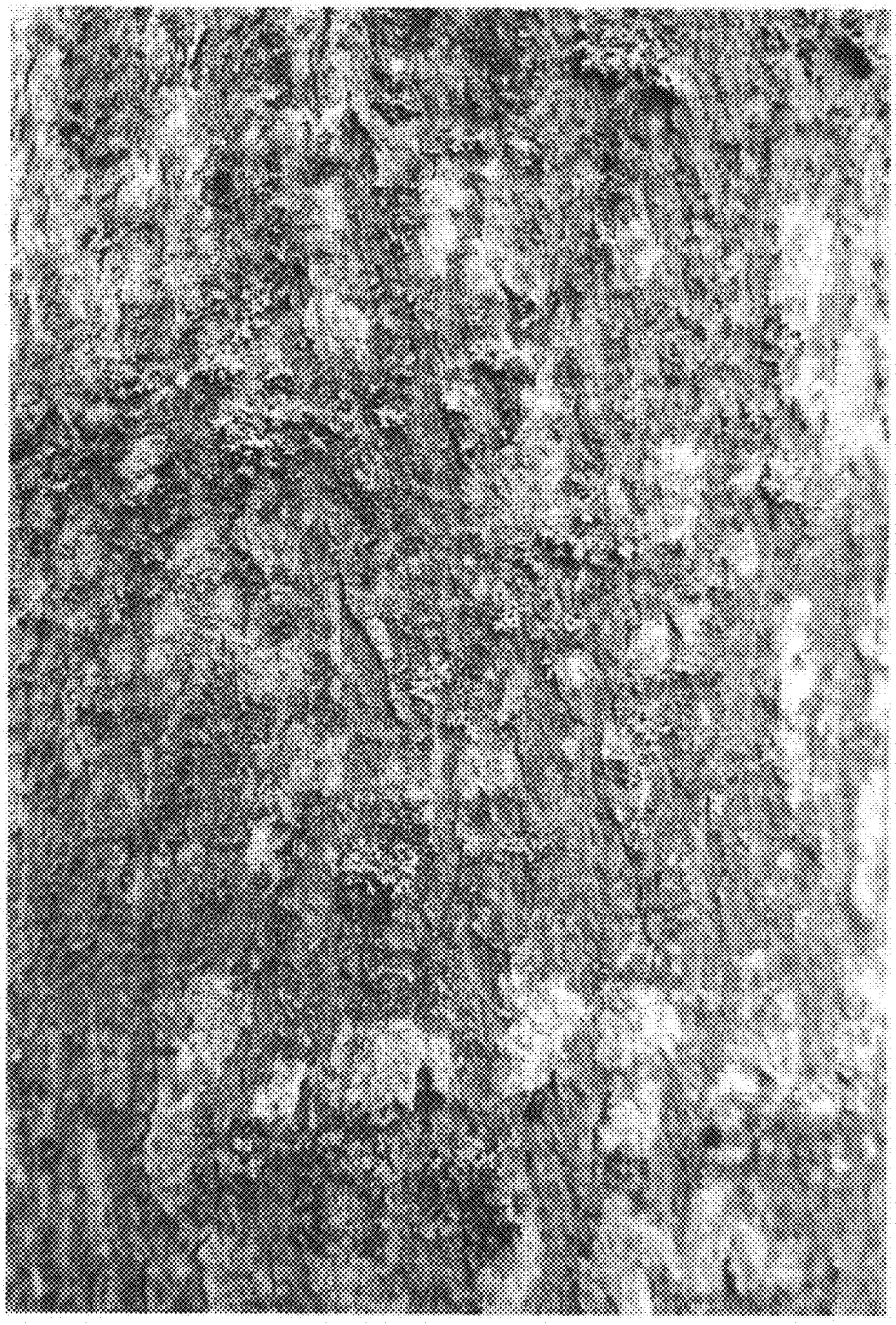
FIG. 10: Shows mature bark on the original tree at 13 years of age.

The following detailed description of the 'JFS-KW249' variety is based on observations of the original tree and one, two, and three year old progeny. The observed progeny were trees which were growing in Boring, Oreg.

The following is a detailed description of my new maple tree with color descriptions using terminology in accordance with The Royal Horticultural Society (London) Colour Chart© 1986, except where ordinary dictionary significance of color is indicated.

Scientific name: *Acer truncatum* 'JFS-KW249'.

Parentage:

*Seed parent*.—A selected seedling of *Acer truncatum* that I designated as Acer truncatum 'KW-201ATR'.

*Pollen parent*.—Unknown.

Tree:

*Overall shape*.—Oval to broadly oval, compact & dense.

*Height*.—5.8 meters at 13 years of age.

*Width*.—4.0 meters at 13 years of age.

*Caliper*.—148 mm at 100 mm height above ground and 115 mm at 1 meter above ground at 13 years of age.

*Trunk*.—Stout, straight.

*Trunk bark texture*.—Slightly rough, vertically fissured.

*Trunk bark color*.—Immature bark color: Greyed Brown 199D to Greyed Green 197D. Mature bark color: Greyed Green 197A on ridges of bark and Greyed Orange 165B in fissures. Lenticels: Rounded 0.5 mm-1.0 mm in diameter Greyed Orange 164C. Disappearing into the bark with age.

*Primary branches*.—Stiffly outward and upwards spreading at 45° to 60° from the vertical trunk.

*Branch color*.—Same as immature bark, Greyed Brown 199D to Greyed Green 197D.

*Branch lenticels*.—Rounded 0.5 mm-1.0 mm. Greyed Orange 164C, disappearing under the bark by the 4$^{th}$ year.

*Dormant buds*.—Ovoid, slightly adpressed against the twig, 4 mm to 5 mm long by 2 mm to 3 mm wide by 1 mm to 2 mm thick, with overlapping scales. Greyed-orange 176A to Greyed-purple 183A.

*Bud break*.—Bud break averages March 25 in Boring, Oreg.

*Internodes*.—Average length 45 mm when measured at the mid-point of a 1 year old tree.

*Hardiness*.—Has tolerated field temperatures to 10 degrees F. without damage in Boring, Oreg. This is the minimum temperature this location experienced during the life of the tree. It is believed to have Zone 5 cold hardiness similar to other plants of this species.

*Disease resistance*.—It has shown moderately good resistance to powdery mildew.

Leaves: Except as otherwise noted, observations are from twenty vigorous growth leaves.

*Arrangement*.—Opposite.

*Type*.—Simple.

*Texture*.—Smooth.

*Sheen*.—Very glossy.

*Length*.—10 cm to 16 cm, averaging 12.6 cm on leaves from 2 year old nursery trees.

*Width*.—13 cm to 18 cm, averaging 14.8 cm on leaves from 2 year old nursery trees.

*Petioles*.—6 cm to 10 cm long, averaging 8.1 cm on leaves from 2 year old nursery trees. Diameter 1.0 mm to 2.0 mm.

*Overall shape*.—Palmate with five major lobes.

*Margin*.—Entire, with 5 major lobes and 5 minor lobes, each lobe tip is acuminate.

*Tip*.—Acuminate.

*Base*.—Truncate to slightly sagittate.

*Stipules*.—None.

*Spring leaf color*.—First emerging leaves Yellow Green 145A in the center with a gradual transition to a tint of Greyed Orange 177A which is deepest along the leaf margins.

*Summer leaf color*.—Upper leaf surface: Green 139A. Lower leaf surface: Green 137A Vein: Yellow Green 145C on the lower shaded surface and Greyed Red 181B to Greyed Red 181C on the upper surface.

*Fall leaf color*.—Leaves in the main crown of the tree range from Greyed Purple 187B to Greyed Purple 185A or Red Purple 59A. Leaves at the branch tips can be slightly a slightly darker Greyed Purple 187A.

*Timing of fall leaf color*.—Average dates for original tree in Boring, Oreg. Onset: October 24$^{th}$ to October 31st (2014 & 2015 in Boring, Oreg.). Peak: November 5th to November 15th (2014 & 2015 in Boring, Oreg.). Latest extent of red fall color: Averages November 25. Fall color begins and peaks at a time that is about one week later than typical for the species.

*Defoliation*.—Complete defoliation averages November 29 in Boring, Oreg.

*Pubescence*.—None.

*Persistence*.—The tree is deciduous.

Flowers:

*Overall*.—Monoecious, flowers held in many flowered corymbs with staminate flowers and perfect flowers occurring in separate cluster on the tree. Most clusters were observed to be male, female flowers are infrequent. Staminate flowers occur in corymbs of 30 to 60 flowers, the corymb is rounded, 6 cm to 8 cm in diameter. Flowers have 10 exerted stamens, Yellow Green 151B. Anthers are yellow 11A. Five petals are present, long oval to long obovate, each 2 mm to 3 mm wide by 5 mm to 6 mm long. Five sepals are present, acute, each 1.5 mm wide by 3 mm to 4 mm long. Pistilate flowers occur in corymbs of typically 15 to 30 flowers. The corymb is rounded, 4 cm to 6 cm in diameter. Flowers have 10 short, 2 mm long, vestigial, nonfunctioning stamens. The pistil is exerted, 3 mm to 4 mm long and divides into a two parted style. The ovary is superior with 2 carpels. Female flowers are 10 mm to 14 mm in diameter with 5 petals and 5 sepals. Petals are long oval to long obovate 2 mm to 3 mm wide by 5 mm to 6 mm long, Yellow 10A. Sepals are acute 1.5 mm by 4 mm to 5 mm long, Yellow Green 151C. The pistil is Yellow Green 151B. Flowering begins about one week after vegetative bud break and continues for about two weeks depending on weather conditions. Average flowering date March 30th to April 5th depending on the year.

Fruit: Samaras are sparsely produced, less than the species. Samaras, held in pairs at angle of 115° to 130°, maturing in mid to late October in Boring, Oreg. Samara pairs typically occur in clusters of two to four. Individual samaras measure 35 to 45 mm long by 10 to 14 mm wide and 5 mm thick at the seed end becoming paper thin along the wing margin. Samara color varies with maturity: Yellow Green 144C to Yellow Green 150C in early October to Greyed Orange 165D to Greyed Yellow 161B in late October.

COMPARISON TO OTHER CULTIVATED VARIETIES

My new variety is easily distinguished from the most similar cultivars by a combination of its more compact growth rate, as evidenced by its lesser height, shorter internode length and a different number of branches along the length of its trunk. In addition the upper leaf surface differs in color. The following table shows these differences as measured on one year old trees growing in Boring, Oreg.

Table 1 defines these differences.

TABLE 1

| Feature: | 'JFS-KW249' | 'JFS-KW187' Patent Pending | 'Warrenred' U.S. Plant Pat. No. 7,433 | 'Keithsform' U.S. Plant Pat. No. 7,529 |
|---|---|---|---|---|
| Tree height | 157 cm | 188 cm | 320 cm | 308 cm |
| Internode length | 5.1 cm | 7.1 cm | 9.5 cm | 9.7 cm |

TABLE 1-continued

| Feature: | 'JFS-KW249' | 'JFS-KW187' Patent Pending | 'Warrenred' U.S. Plant Pat. No. 7,433 | 'Keithsform' U.S. Plant Pat. No. 7,529 |
|---|---|---|---|---|
| Branches* | 6.2 | 13.2 | 7.5 | 1.2 |
| Leaf color, top | Green 139A to Yellow-green 145A | Green 139A to Yellow-green 147A | Yellow-green 146A to Green 137A Green 137B | Yellow-green 147B to Green and 137A |

*Average number of branches over 20 cm in length along the trunk

COMPARISON TO THE PARENT SPECIES

My new tree differs from standard (unpatented) *Acer truncatum* in that my new variety is more robust in growth and size, as evidenced by larger leaves and longer internode length. Additionally, its leaf color differs. Differences are shown in Table 2, below.

TABLE 2

| Feature | 'JFS-KW249' | *Acer truncatum* |
|---|---|---|
| Leaf width | 12.6 cm | 9.0 cm |
| Leaf length | 14.8 cm | 9.8 cm |
| Leaf color, summer upper surface | Green 139A to Yellow-green 145A | Yellow-green 144A to 147A |
| Internode length | 5.1 cm | 4.1 cm |

I claim:

1. A new and distinct variety of maple tree, substantially as herein illustrated and described.

* * * * *